(12) United States Patent
Geiger et al.

(10) Patent No.: US 8,433,389 B2
(45) Date of Patent: Apr. 30, 2013

(54) SURGERY ASSISTANCE SYSTEM FOR GUIDING A SURGICAL INSTRUMENT

(76) Inventors: Robert Geiger, Metten (DE); Jürgen Scherr, Tiefenbach (DE)

( * ) Notice: Subject to any disclaimer, the term of this patent is extended or adjusted under 35 U.S.C. 154(b) by 312 days.

(21) Appl. No.: 12/935,012

(22) PCT Filed: Mar. 20, 2009

(86) PCT No.: PCT/DE2009/000387
§ 371 (c)(1),
(2), (4) Date: Sep. 28, 2010

(87) PCT Pub. No.: WO2009/117989
PCT Pub. Date: Oct. 1, 2009

(65) Prior Publication Data
US 2011/0028992 A1 Feb. 3, 2011

(30) Foreign Application Priority Data
Mar. 28, 2008 (DE) .......................... 10 2008 016 146

(51) Int. Cl.
*A61B 19/00* (2006.01)
(52) U.S. Cl.
USPC ........... 600/407; 600/424; 606/130; 606/103; 606/1; 901/2; 901/3; 901/33; 73/862.04
(58) Field of Classification Search .................. 700/245, 700/263, 262; 600/102, 118, 130, 424, 407; 600/109, 427, 101, 229, 103, 117; 901/2, 901/47, 33, 3, 34, 41; 709/208; 606/130, 606/1, 103; 73/862.04, 540.03
See application file for complete search history.

(56) References Cited

U.S. PATENT DOCUMENTS

| 5,911,036 | A | 6/1999 | Wright et al. |
| 6,024,695 | A | 2/2000 | Taylor |
| 6,120,433 | A | * | 9/2000 | Mizuno et al. ................ 600/102 |

(Continued)

FOREIGN PATENT DOCUMENTS

| DE | 103521971 | A1 | 8/2005 |
| DE | 1020040527531 | A1 | 5/2006 |
| WO | WO 03/041057 | A2 | 11/2002 |

OTHER PUBLICATIONS

Navab, Nassir et al, Visual Servoing for Automatic and Uncalibrated Needle Placement for Percutaneous Procedures, IEEE, 2000.

*Primary Examiner* — Ronnie Mancho
(74) *Attorney, Agent, or Firm* — Welsh Flaxman & Gitler LLC

(57) ABSTRACT

The invention relates to a surgery assistance system for guiding a surgical instrument. The surgical instrument (3) is fastened lo an arm system (10, 12, 14), the tip (S) of the surgical instrument (3) can be moved in a controlled manner by means of the arm system (10, 12, 14) in a Cartesian patient coordinate system (PKS), one of the three spatial axes (x, y, z) of the Cartesian patient coordinate system (PKS) extends through the surgical opening or the trocar point (T) receiving the surgical instrument (3). Advantageously, the angle of inclination (w) of the surgical instrument (3) is determined with respect to the spatial axis (z) of the Cartesian patent coordinate system (PKS) extending through the trocar point (T), the angle of inclination (w) so determined is compared with a predetermined set angle of inclination (ws) for the purpose of guiding the tip (S).

18 Claims, 6 Drawing Sheets

U.S. PATENT DOCUMENTS

| | | | |
|---|---|---|---|
| 6,201,984 B1 * | 3/2001 | Funda et al. | 600/407 |
| 6,468,265 B1 * | 10/2002 | Evans et al. | 606/1 |
| 7,447,537 B1 * | 11/2008 | Funda et al. | 600/424 |
| 8,160,678 B2 * | 4/2012 | Cropper et al. | 600/427 |
| 2002/0133173 A1 * | 9/2002 | Brock et al. | 606/130 |
| 2003/0187351 A1 | 10/2003 | Franck et al. | |
| 2005/0107808 A1 * | 5/2005 | Evans et al. | 606/139 |
| 2005/0183532 A1 | 8/2005 | Najafi et al. | |
| 2007/0088247 A1 * | 4/2007 | Bliweis et al. | 604/22 |
| 2007/0173977 A1 | 7/2007 | Schena | |
| 2009/0024142 A1 * | 1/2009 | Ruiz Morales | 606/130 |
| 2010/0094312 A1 * | 4/2010 | Ruiz Morales et al. | 606/130 |
| 2010/0222647 A1 * | 9/2010 | Hashimshony et al. | 600/301 |

* cited by examiner

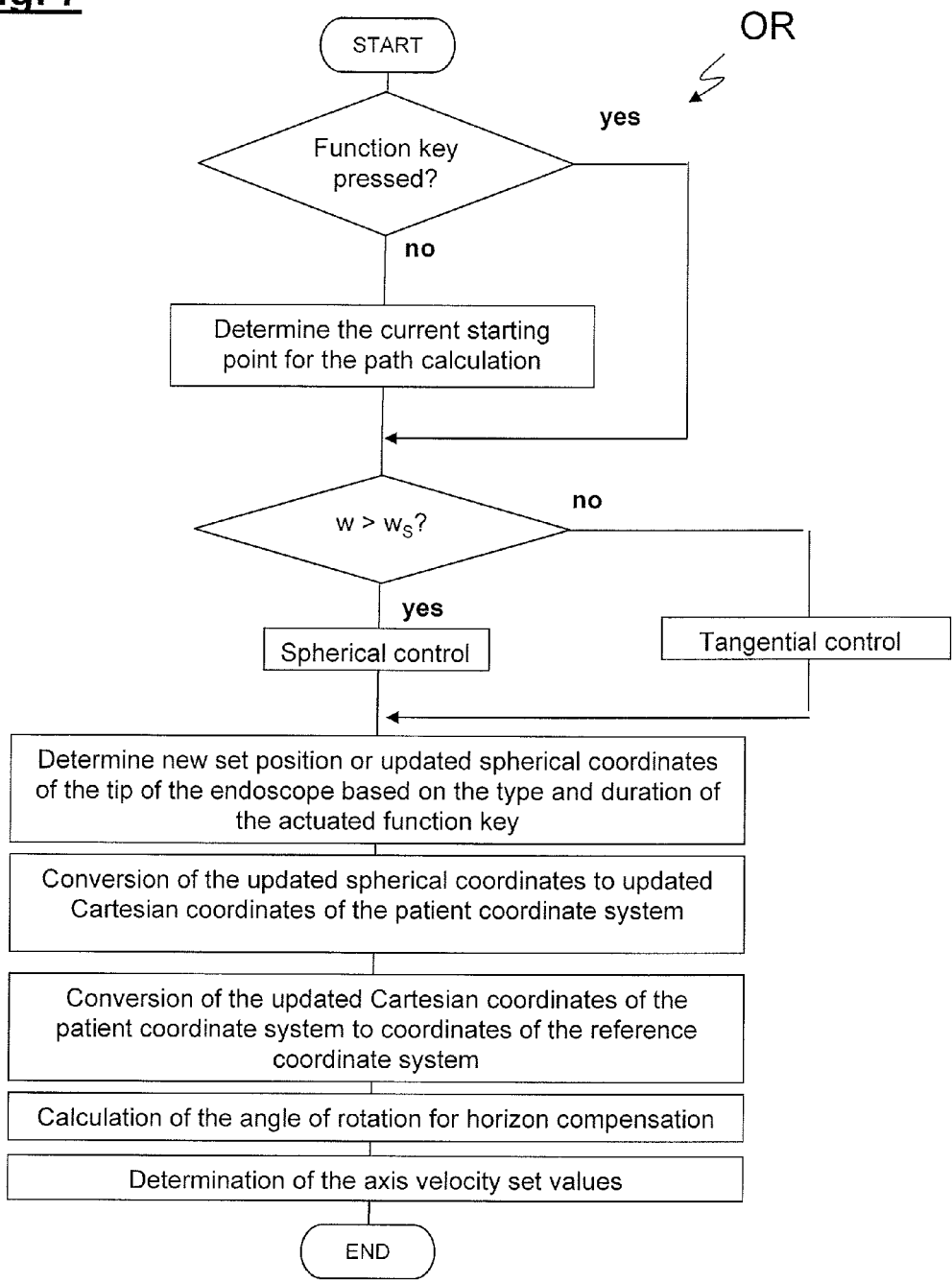

SURGERY ASSISTANCE SYSTEM FOR GUIDING A SURGICAL INSTRUMENT

BACKGROUND OF THE INVENTION

The invention relates to a surgery assistance system for guiding a surgical instrument, in particular a camera system comprising an endoscope dependant on manual actuation of at least one function key of a control element.

Document DE 103 52 197, for example, describes a surgery assistance system which is used during minimally invasive surgery for guiding surgical instruments, such as camera systems.

Document DE 10 2004 052 753 A1 describes a method for controlling the guiding of at least one surgical instrument in relation to a guiding surgical instrument by means of a surgery assistance system, in which during minimally invasive surgery the current position data of a first sensor element in a three-dimensional measuring space are determined, the first sensor element being provided on a section of the guiding surgical instrument protruding from the patient's body. Based on the measured position data of the guiding surgical instrument, the position data of the guided surgical instrument is calculated and the latter is guided by means of the surgery assistance system.

The publication "Visual Serving for Automatic and Uncalibrated Needle Placement for Percutaneous Procedures" by Nassir Navab et. al., IEEE, 2000 describes a method for the image-controlled guiding of a needle or a surgical instrument in the framework of a percutaneous surgical procedure in which the current position of the guided needle or of the guided surgical instrument is displayed to the surgeon by means of an imaging process.

Document WO 03/041057 A2 describes a system and a corresponding method for image-controlled guiding of an instrument by means of a robot unit or a robot arm, on which a guided instrument is provided. A system for guiding a surgical instrument during surgical operations, in particular spinal operations, is disclosed in US 2003/0187351.

The disadvantage of the prior art surgery assistance systems is that they are limited with respect to the work space of the instrument which is motor guided by the surgery assistance system.

It is an object of the invention is to present a surgery assistance system for guiding a surgical instrument, in particular a camera system comprising an endoscope characterized by more precise guiding of the instrument, an enlarged work space for the guided surgical instrument and a high degree of user friendliness.

SUMMARY OF THE INVENTION

An essential aspect of the surgery assistance system according to the invention is the fact that a control and analysis routine is provided, which is designed for determining the angle of inclination of the surgical instrument in relation to the spatial axis of the Cartesian patient coordinate system extending through the trocar point and for comparing the angle of inclination so determined with a predetermined set angle of inclination, whereby if the determined angle of inclination exceeds the set angle of inclination the tip of the surgical instrument is guided on a semi-spherical surface receiving the tip and when the determined angle of inclination is below the set angle of inclination the tip of the surgical instrument is guided along a tangent extending through the tip of the surgical instrument on the semi-spherical surface.

In an advantageous variant of the surgery assistance system according to the invention, when the determined angle of inclination exceeds the set angle of inclination the tip of the instrument is guided on a circular path which concentrically surrounds the trocar point.

Advantageously, the set angle of inclination is between 10° and 25°, preferably between 15° and 20°. This enables precise guiding of the surgical instrument also in the case of extremely low angles of inclination, in addition to a longitudinal axis of the instrument extending essentially perpendicular to the x-y plane. After the tip of the instrument reaches a sufficient distance from the z-axis of the Cartesian patient coordinate system, the surgery assistance system automatically switches from tangential control to spherical control. The guiding path for guiding the tip of the surgical instrument in the patient's body is calculated based on the selected control type.

BRIEF DESCRIPTION OF THE DRAWINGS

The invention is described below in detail based on an exemplary embodiment with reference to the drawings, in which:

FIG. 7 shows a flow diagram of a surgical routine.

DETAILED DESCRIPTION OF THE INVENTION

Figure 1:
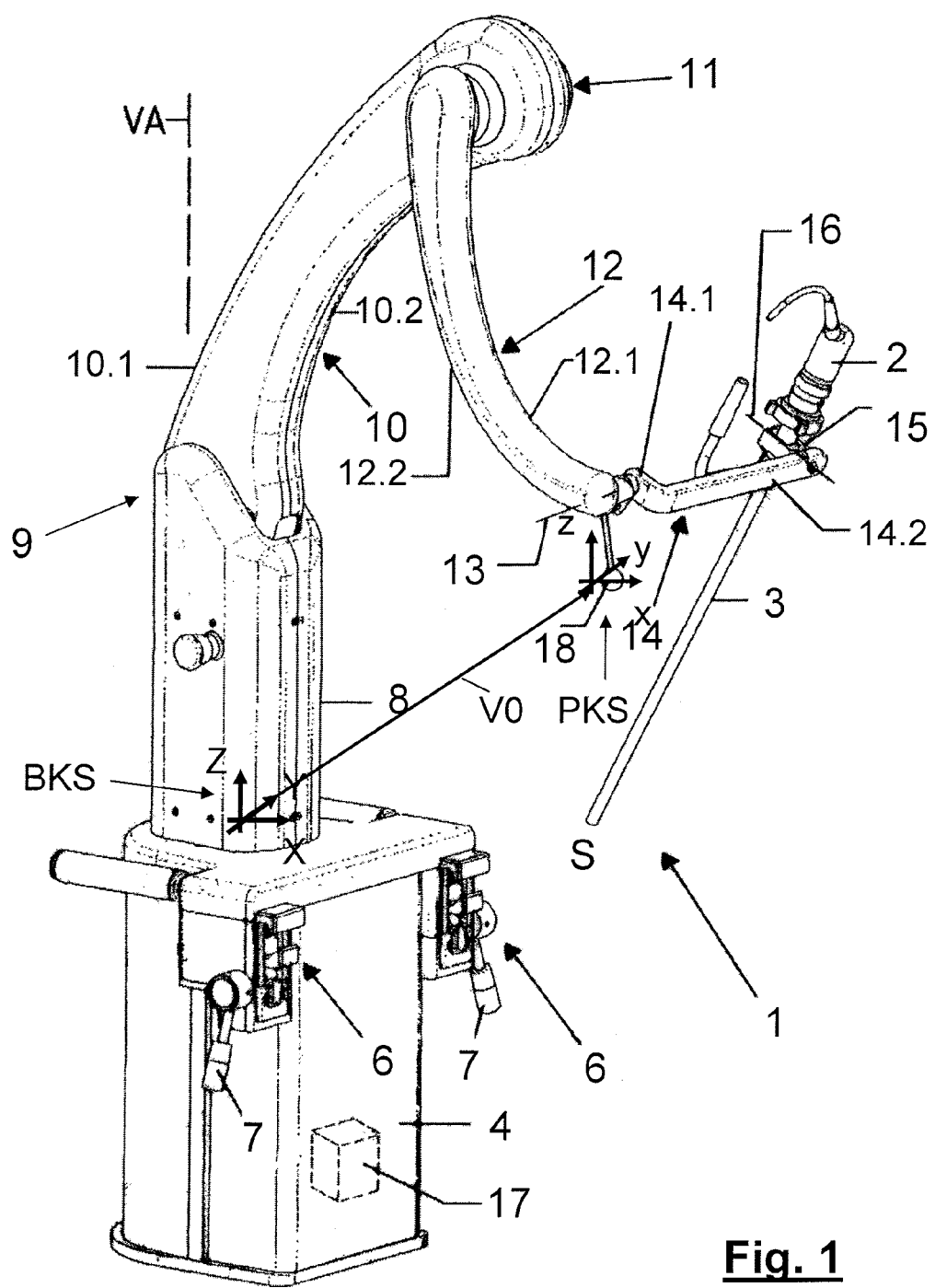
FIG. 1 shows a surgery assistance system in a perspective view.

The surgery assistance system for medical interventions, in particular minimally invasive surgery, designated 1 in FIG. 1, is designed for guiding surgical instruments, for example for guiding a camera system 2 comprising an endoscope 3. The surgical instrument, in particular the endoscope 3 of the camera system 2, is inserted through a small surgical opening ("trocar") or trocar point T into a surgical space 19 within a patient's body 20.

The surgery assistance system 1 comprises a housing 4 in which the essential functional and control elements are accommodated and which for example can be fastened on the side of an operating table 5, namely in the depicted embodiment by means of two manually actuated clamping devices 6, which are provided mutually offset from one another on one common side of the housing 4 and for the actuation of which a swivel lever 7 is provided. For controlling the surgery assistance system 1 and for processing the image data generated by the camera system 2 the surgery assistance system 1 is connected to a computer system CS.

A support column 8 protrudes over the top of the housing 4 of the surgery assistance system 1 and can be rotated and swiveled on a vertical axis VA by means of an electric motor drive (not depicted in the drawings) accommodated in the housing 4. In the area of the upper end of the support column 8, the lower end of one inner arm 10 is coupled to the column by means of a joint 9.

The joint 9, consisting essentially of a hinge pin and corresponding bearings, is designed so that the arm 10 extends with its lower end into the upper, open end of the support column 8, where it is enclosed by the support column 8 in a fork-like manner. The arm 10, which is designed as a hollow body from a lightweight but stable material, e.g. from fiber-reinforced plastic, for example fiberglass-reinforced or carbon-reinforced plastic, is curved in the longitudinal direction of the arm, namely convex on the top side 10.1 of the arm and concave on the bottom side 10.2 of the arm.

On the end of the arm 10 located at a distance from the support column 8 the outer arm 12 is coupled by means of a joint 11. The joint 11 consists essentially of bearing elements and a hinge pin, which leads out of the arm 10 on both ends. With one end of the hinge pin leading out of the arm 10 the one end of the arm 12 is connected in a suitable manner by means of a connecting system (not depicted) so that it cannot rotate but can be removed. The arm 12, which is likewise designed as a hollow body from a lightweight but stable material, e.g. from fiber-reinforced plastic, for example fiberglass-reinforced or carbon-reinforced plastic, is curved in the longitudinal direction of the arm, namely concave on the top side 12.1 of the arm and convex on the bottom side 12.2 of the arm.

On the end of the arm 12 located at a distance from the arm 10 the shorter leg 14.1 of an L-shaped tool holder 14 is mounted freely rotatable by means of a further joint 13, namely on an axis parallel to the longitudinal extension of the longer leg 14.2 of this tool holder 14. On the end of the longer leg 14.2 located at a distance from the shorter leg 14.1 a tool mount 15 designed as a clip is provided on the tool holder 14, on which (tool mount) the endoscope 3 is releasably fastened by locking into position and which can turn and swivel by means of a joint 16 on an axis perpendicular to the axis of the joint 13.

In the depicted embodiment the swivel axes of the joints 9, 11 and 13 are parallel or essentially parallel horizontal or essentially horizontal axes oriented to one other. The joints 13 and 16 are free joints, i.e. these joints enable free swiveling of the tool holder 14 relative to the arm 12 and of the mount 15 relative to the tool holder 14. The joints 9 and 11 on the other hand respectively form controlled axes for the controlled hydraulically actuated swivel movements, namely by means of a hydraulic drive, which is controlled by means of a control apparatus 17 accommodated in the housing 4. The control apparatus 17 is provided for the generation of control signals for controlling the various drives of the kinematics of the surgery assistance system 1 in a Cartesian coordinate system. The Cartesian coordinate system with the spatial axes X, Y, Z allocated to the kinematics of the surgery assistance system 1 is referred to hereinafter as the reference coordinate system BKS.

For calibrating the zero or starting position of the surgery assistance system 1 or of the endoscope 3 in relation to the surgical opening or the trocar point T through which the endoscope 3 is to be inserted into the surgical space 19, a rod-shaped registration sensor 18 is provided on the free end of the arm 12, which (sensor) comprises a spherical head on its end standing away from the arm 12. The spherical head of the registration sensor 18 immovably provided on the arm 12 has a defined position in relation to the reference or starting positions of the controlled axes of the surgery assistance system 1 or to the reference coordinate system BKS. Prior to the surgery, the surgery assistance system 1 is registered by guiding the registration sensor 18 to the area of the patient already placed on the OR table at which the surgical opening or the trocar point T is provided for insertion of the endoscope 3. This defines a patient coordinate system PKS, which has a predetermined offset vector V0 to the reference coordinate system BKS. The Cartesian coordinates X0, Y0, Z0 of the offset vector V0 in the reference coordinate system BKS are preferably saved in the control apparatus 17.

Figure 2:
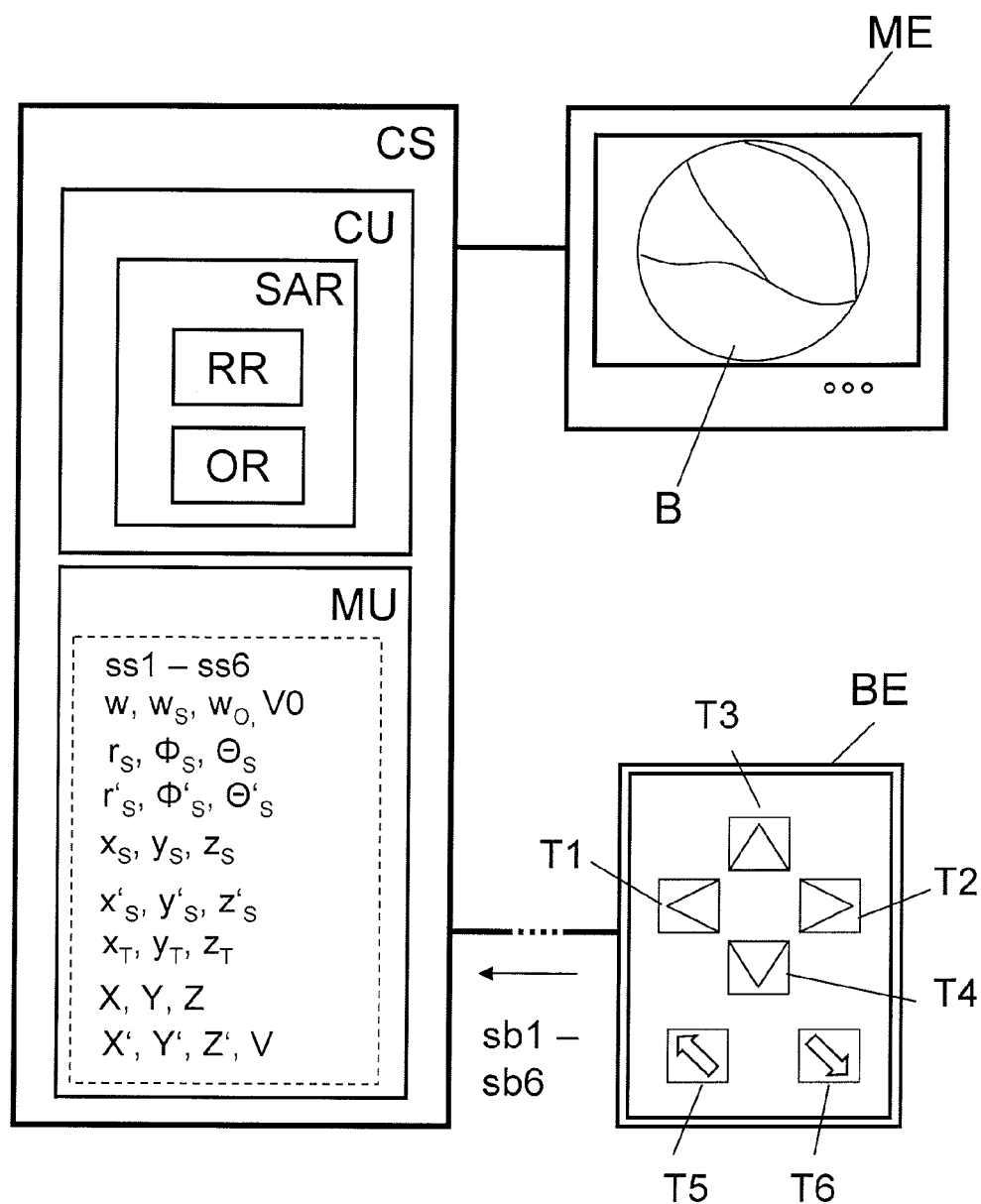
FIG. 2 shows a schematic block diagram of a computer system with a connected control element and monitor unit.

For controlling the movement of the surgical instrument, in particular the endoscope 3 of the surgery assistance system 1, at least one control element BE is provided, which can be designed for example as a foot switch, joystick or hand-operated control. FIG. 2 shows such a control element BE, which for example has six function keys T1-T6. The control element BE is connected to the computer system CS, which comprises at least one control unit CU and one memory unit MU.

For analysis and processing of the image data generated by the camera system 2 and for control of the movement of the instrument, in particular the endoscope 3, by means of the control element BE, the computer system CS is connected with the control apparatus 17 and the camera 2 of the surgery assistance system 1, namely preferably via interface units not depicted in the drawings or via a bus system, for example a CAN bus system.

For display of the images B generated by the camera system 2 and transmitted to the computer system CS for processing, a monitor unit ME is connected to the computer system CS. The image B recorded by the camera system 2 using the endoscope 3 is displayed on the monitor unit ME and shows the user of the surgery assistance system 1 the area of the surgical space 19 located in front of the tip S of the endoscope 3.

During startup and registration of the surgery assistance system 1 the image horizon of the image B displayed on the monitor unit ME is adjusted by rotating the camera system 2 on its longitudinal axis L so that this corresponds to the natural view of the user. The offset angle $w_O$ manually set in this way is recorded by a control and analysis routine SAR executed in the control unit CU and saved in the memory unit MU. The measured offset angle $w_O$ ensures that the image horizon of the image B displayed on the monitor unit ME remains essentially constant during guiding of the endoscope 3 in the surgical space 19.

The control and analysis routine SAR is designed so that the control commands sb1-sb6 generated by the control element BE by actuating the function keys T1-T6 are converted into corresponding control signals ss1-ss6 for controlling the movement of the endoscope 3 of the surgery assistance system 1, which are supplied to the control apparatus 17 for driving its arm system 10, 12, 14 on the respective allocated axes or joints 9, 11, 13, 16. For this purpose, the set positions to be approached by the individual arms 10, 12, 14 are first calculated in the reference coordinate system BKS with the three spatial axes X, Y, Z.

The control element BE comprises for example a first function key T1 for rotating the image B displayed on the monitor unit ME in the direction of the left image edge, a second function key T2 for rotating the image B in the direction of the right image edge and a third and fourth function key T3, T4 for rotating the image B toward the top and bottom image edge. Additionally, a fifth and sixth function key T5, T6 are provided for zooming the displayed image B, namely in that the endoscope 3 is moved further into the surgical space 19 upon actuating the fifth function key T5 and is moved out again by actuating the sixth function key T6. Therefore, the operator of the surgery assistance system 1 can achieve up to 360° rotation of the endoscope 3 within the surgical space 19 by corresponding actuation of the first through sixth function keys T1-T6 of the control element BE, thereby tilting the endoscope 3 by up to 100° in relation to the spatial axis z of the Cartesian patient coordinate system PKS extending through the trocar point and penetrating the surgical space 19 by a depth of up to ca. 300 mm.

In order to enable highly precise guiding of the endoscope 3 by means of the function keys T1-T6, exact knowledge of the set positions of the individual movement axes of the arm system 10, 12, 14 in relation to a starting point, namely the trocar point T, is necessary. For this purpose, single sensors allocated to the different movement axes are used to store the coordinates of the joints 9, 11, 13, 15 of the arm system 10, 12, 14 in relation to the reference coordinate system BKS in the trocar point T as the starting position. The trocar point T also represents the origin of the Cartesian patient coordinate system PKS with the spatial axes x, y, z, i.e. the Cartesian coordinates xT-0, yT-0, zT-0 of the three spatial axes x, y, z of the Cartesian patient coordinate system PKS are allocated to the trocar point T.

The Cartesian coordinates $x_T$, $y_T$, $z_T$ of the determined trocar point T also represent the middle point M of a spherical coordinate system provided for guiding the instrument or the endoscope 3 during the surgery, i.e. in a surgery mode. The spherical middle point M of a spherical surface spanned by the respective spherical coordinates $\phi$, $\ominus$ of the spherical coordinate system corresponds to the trocar point T. The tip S of the endoscope 3 opposite the camera system 2 rests on the spherical surface or semi-spherical surface TG, which is spanned by its spherical coordinates $r_S$, $\phi_S$, $\ominus_S$.

The distance $r_S$ of the tip S from the trocar point T, i.e. the penetration length of the endoscope 3 into the surgical space 19, is defined by the spherical coordinate rs. The spherical coordinate $\phi$s defines the angle of rotation, counter-clockwise, around the z-axis of the Cartesian coordinate system, namely in relation to the x-axis of the Cartesian coordinate system. The spherical coordinate $\theta_S$ of the tip S of the endoscope 3 corresponds to the sum of the angle of inclination w of the longitudinal axis L of the endoscope 3 in relation to the z-axis of the Cartesian patient coordinate system PKS and an angle of +/−180°.

Figure 3:
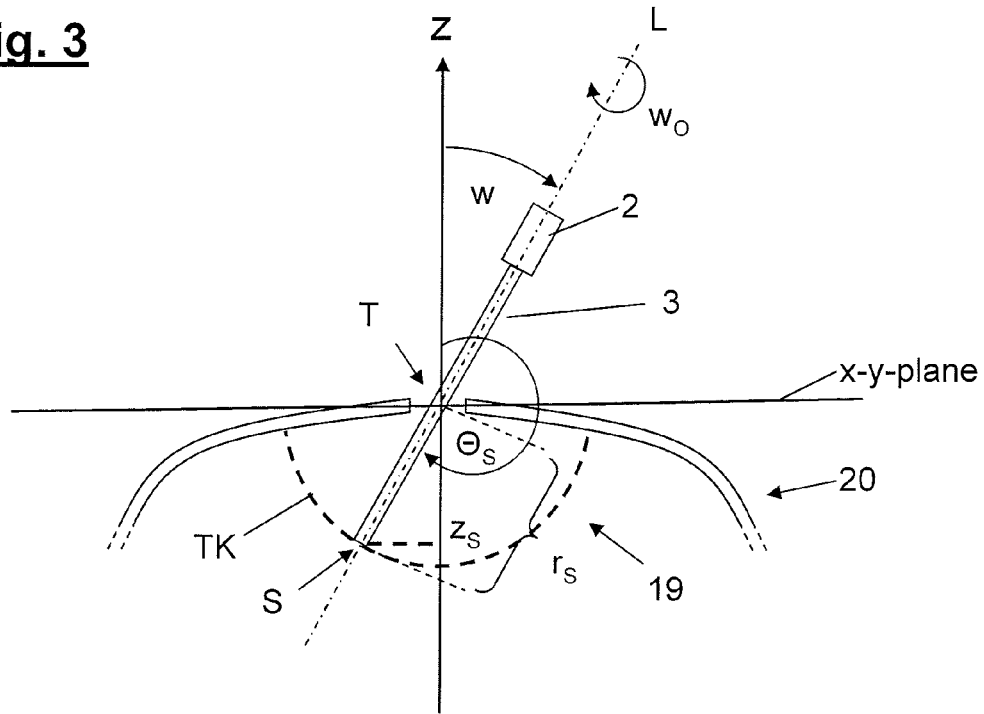
FIG. 3 shows a cross section through a patient's body in which the tip of an endoscope of a camera system is inserted into the surgical space.

FIG. 3 shows a schematic side view of an endoscope 3 inserted into the surgical space 19 of the patient's body 20 through the trocar point T, whereby the origin of the Cartesian patient coordinate system PKS corresponds to the trocar point T. In FIG. 3 the z-axis of the Cartesian patient coordinate system PKS therefore is in the plane of projection and the x-y plane of the Cartesian patient coordinate system PKS extends perpendicular to the plane of projection. The patient's body 20 is on the OR table 5 with a lying surface which is parallel to the x-y plane, whereby the x-y plane is spanned by the spatial axes x, y of the Cartesian patient coordinate system PKS.

Figure 4:
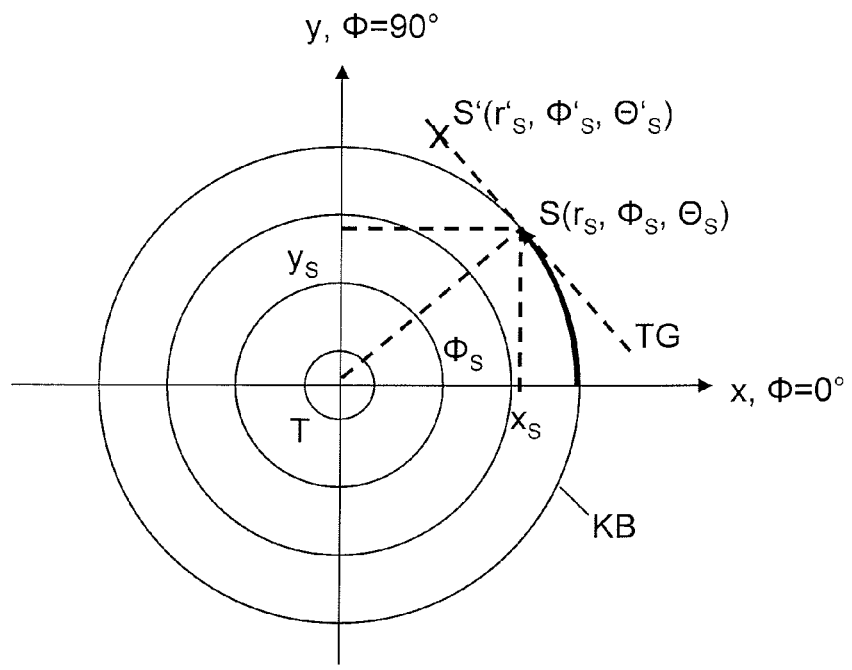
FIG. 4 shows a top view onto the x-y plane of a Cartesian patient coordinate system in the case of guiding the tip of an endoscope along a tangent.

The longitudinal axis L of the instrument or of the endoscope 3 extends through the trocar point T and therefore through the zero point of the Cartesian patient coordinate system PKS and encloses with the y-axis an angle of inclination w, the angle of inclination w in surgery mode being between 0° and 100°. A view from above of the x-y plane of the Cartesian patient coordinate system PKS shown in FIG. 3 is depicted exemplarily in FIG. 4; FIGS. 3 and 4 show both the Cartesian coordinates $x_S$, $y_S$, $z_S$ of the tip S of the endoscope 3 in the patient coordinate system PKS and the corresponding spherical coordinates $r_S$, $\phi_S$, $\theta_S$ of the tip S of the endoscope 3 in the spherical coordinate system.

Figure 5:
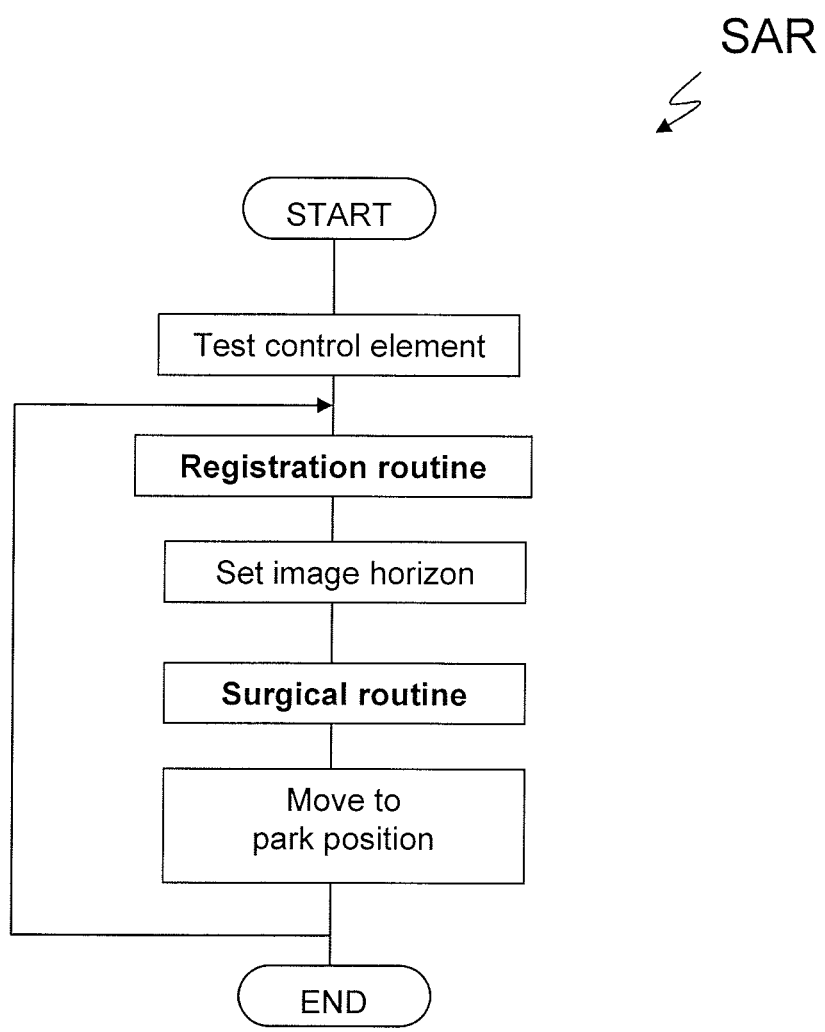
FIG. 5 shows a flow diagram of an analysis and control routine for controlling the surgery assistance system.

The following description explains the controlling of the guiding of the surgical instrument 3 by means of the surgery assistance system 1 by a control and analysis routine SAR executed in the control unit CU. FIG. 5 exemplarily shows the single steps of the control and analysis routine SAR in a flow diagram.

After the control and analysis routine SAR is started, the control element BE is checked to ensure it is functioning properly and then a registration routine RR is executed for registration of the surgery assistance system 1. Registration of the surgery assistance system 1 or of the arm system 10, 12, 14 takes place by mapping the Cartesian reference coordinate system BKS, which is predetermined by the three spatial axes X, Y, Z with six directions of movement +/−X, +/−Y, +/−Z, to the respective trocar point T. This defines the patient coordinate system PKS. The control commands sb1-sb6 generated by actuation of the first through sixth function keys T1-T6 are mapped by the registration routine RR into movements of the arm system 10, 12, 14 along the six directions of movement +/−X, +/−Y, +/−Z.

After execution of the registration routine RR or after mapping of the origin of the Cartesian reference coordinate system BKS to the trocar point T, the arm system 10, 12, 14 of the surgery assistance system 1 is moved for example into a waiting position.

In the waiting position or after insertion of the endoscope 3 into the surgical space 19, the image horizon of the image displayed on the monitor unit ME is calibrated, namely by rotating the camera system 2 on its longitudinal axis L. Calibration can take place either manually or electronically, for example by means of an allocated drive unit. The calibrated angle of rotation in relation to the current set positions of the axes of the arms system 10, 12, 14 is saved in the memory unit MU as the offset angle $w_O$. For example, the edge of the image B to be displayed on the monitor unit ME can be edited using an image processing software so that during guiding of the endoscope 3 in the surgical space 19 the image horizon of the image B displayed on the monitor unit ME remains essentially constant.

After setting the image horizon the surgery assistance system 1 is switched to surgery mode. To do this, the surgical routine OR is executed by the control and analysis routine SAR. After completion of the surgery, the arm system 10, 12, 14 of the surgery assistance system 1 is moved to a predetermined park position and, if applicable, the control and analysis routine SAR is executed again in a different trocar point T.

Figure 6:
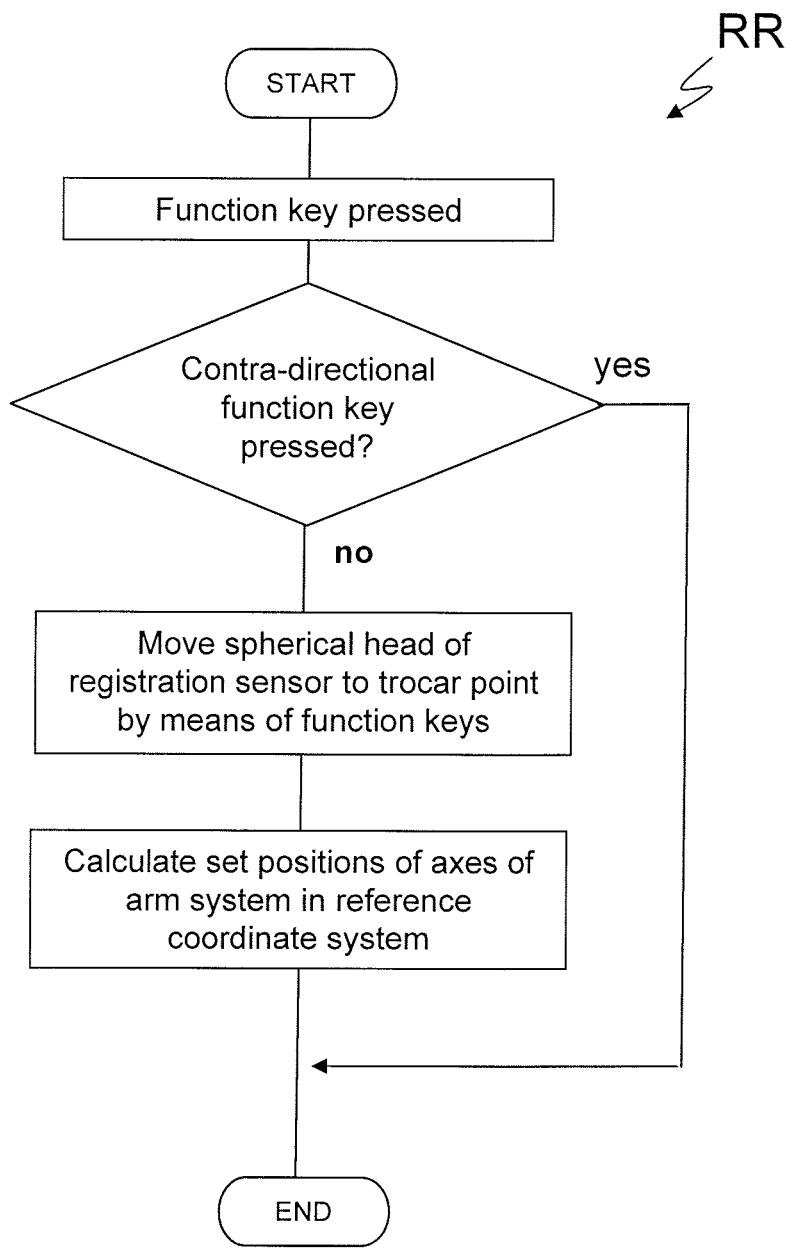
FIG. 6 shows a flow diagram of a registration routine.

FIG. 6 exemplarily shows a flow diagram of the registration routine RR.

If the registration routine RR detects that one of the six function keys T1-T6 is pressed, the next step determines whether a contra-directional function key T1-T6 is simultaneously pressed. If, for example, the first and second function keys T1, T2 are pressed simultaneously, the arm system 10, 12, 14 is not actuated. This ensures that a defective key or pressing of contra-directional keys is promptly detected by the control and analysis routine SAR so that suitable safety measures can be initiated, for example automatic shutdown of the drives.

For setting the trocar point 1 and therefore for registration of the surgery assistance system 1 the spherical head of the registration sensor 18 is guided into the trocar point T of the patient's body 20 on the OR table 5, namely by actuation of the corresponding function keys T1-T6. Afterwards, the set positions of the axes of the arm system 10, 12, 14 in the Cartesian reference coordinate system BKS are calculated in the control and analysis routine SAR based on the calibrated zero or starting position, namely using the offset vector V0. The surgery assistance system 1 is now registered in relation to the trocar point T.

In surgery mode, the surgical routine OR is executed in the control unit CU. The surgical instrument, in particular the camera system 2 comprising an endoscope 3, is guided preferably cyclically, i.e. at the cycle periods defined by the preferably digital control unit CU.

In a first step it is determined whether at least one of the function keys T1-T6 is pressed. If this is the case, the surgical routine OR guides the tip S of the endoscope 3 along the calculated path based on the path position last saved. However, if none of the function keys T1-T6 is pressed by the user, then a current calculation of the coordinates of the starting point of the subsequent path is conducted, namely of the coordinates $x_S$, $y_S$, $z_S$ of the tip S of the instrument or endoscope 3 in the Cartesian patient coordinate system PKS. The currently determined or already saved coordinates $x_S$, $y_S$, $z_S$ of the tip S of the endoscope 3 are then converted to the corresponding spherical coordinates $r_S$, $\phi_S$, $\theta_S$ of the allocated spherical coordinate system. The required conversion formulas are sufficiently known in the art.

Based on the determined spherical coordinates $r_S$, $\phi_S$, $\theta_S$ of the tip S the angle of inclination w of the endoscope 3 in relation to the z-axis of the Cartesian patient coordinate system PKS is determined, which can be between approximately 0° and 100°. The determined angle of inclination w is compared with a selected set angle of inclination $w_S$ which is stored in the memory unit MU and is between 10° and 25°, preferably between 15° and 20°.

If the angle of inclination w exceeds the set angle of inclination $w_S$, the tip S of the endoscope 3 is guided on a path, preferably a circular path KB, extending through the semi-spherical surface TK spanned by the spherical coordinates $r_S$, $\phi_S$, $\theta_S$. Based on the actuation of the first through fourth function key T1 through T4, the tip S is accordingly guided in the respective selected direction of movement on the semi-spherical surface TK or on the respective circular path KB. During the spherical control the tip S of the endoscope 3 moves on longitudes and latitudes similar to circular paths on the semi-spherical surface TK spanned in the surgical space 19, the planes of said semi-spherical surface being perpendicular or parallel to the x-y plane. Actuation of the first or second function key T1, T2 corresponds to a leftward or rightward movement on a circular path extending concentrically around the z-axis (see FIG. 4) and therefore approximately to a leftward or rightward movement of the image B displayed on the monitor unit ME. Analogously, actuation of the third or fourth function key T3, T4 corresponds to an upward or downward movement on a circular path KB extending perpendicular to the x-y plane.

If the determined angle of inclination w is below the set angle of inclination $w_S$, the tip S of the endoscope 3 is guided along a tangent TG extending through the tip S of the endoscope 3 and resting on the semi-spherical surface TK. During tangent guiding, the tip S of the endoscope 3 is moved based on the current position of the tip S, which also determines the image rotation and therefore the image horizon, tangentially to the semi-spherical surface TK spanned in the surgical space 19, namely along the direction of the two main axes of the rotated image B. The movements of the tip S, in case of continuous leftward or rightward guiding, i.e. continuous actuation of the first or second function key T1, T2, do not describe a circular path, but rather a spiral path of movement. Upward or downward control takes place analogously to the spherical control on a circular path extending perpendicular to the x-y plane.

This results in at least two different control types for determining a new set position, i.e. of the updated spherical coordinates $r'_S$, $\phi'_S$, $\theta'_S$ of the tip S of the endoscope 3 to be approached by the drive system on a predetermined path of movement defined by the control type, i.e. based on the determined angel of inclination w the determined path of movement will be calculated differently as a result of actuation of one of the first four function keys T1 to T4. The new set position or the updated spherical coordinates $r'_S$, $\phi'_S$, $\theta'_S$ to be approached will be stored in the memory unit MU if applicable.

Actuation of the fifth and sixth function keys T5, T6 achieves in both cases for example a decrease or an increase of the radius rs of the semispherical element. The determination of the updated spherical coordinates $r'_S$, $\phi'_S$, $\theta'_S$ of the tip S on the predetermined path of movement further depends on the type and duration of actuation of the first through fourth function keys T1-T4.

Afterwards, the updated coordinates $x'_S$, $y'_S$, $z'_S$ of the tip S' in the Cartesian patient coordinate system PKS are determined for the spherical coordinates $r'_S$, $\phi'_S$, $\theta'_S$ of the tip S' and converted to updated coordinates $X'_S$, $Y'_S$, $Z'_S$ of the tip S' in the Cartesian reference coordinate system BKS. Based on this the respective axis velocities V for controlling the drives of the arm system 10, 12, 14 are determined. If necessary, the angle of rotation of the camera system 2 on the longitudinal axis L is adjusted based on the stored offset angle $w_O$ for compensation of the image horizon.

The invention was described above based on an exemplary embodiment. It goes without saying that numerous modifications and variations are possible, without abandoning the underlying inventive idea on which the invention is based.

For example it is possible to set several trocar points T and to change between them. Furthermore, for ensuring the safety of the surgery assistance system 1, in addition to preventing contra-directional actuation of the function keys T1-T6, it is possible to provide a central power switch for central switching of the power required for operation of the drives.

In addition, the control and analysis routine SAR can be provided with an image processing routine for the optical detection of a rotating collision of the tip S of the endoscope 3 with the tissue present in the surgical space 19, which for example analyzes the light/dark contrasts in the generated image and the change in these over time.

REFERENCE LIST

1 surgery assistance system
2 camera system
3 endoscope
4 housing
5 OR table
6 clamping device
7 swivel lever
8 support column
9 joint
10 arm
10.1 top of arm
10.2 bottom of arm
11 joint
12 arm
12.1 top of arm
12.2 bottom of arm
13 joint
14 tool holder
14.1 shorter leg
14.2 longer leg
15 mount
16 joint
17 control apparatus 18 registration sensor
19 surgical space
20 patient's body
B image
BE control element
BKS Cartesian reference coordinate system
CS computer system
CU control unit
L longitudinal axis
ME motor unit
MU memory unit
OR surgical routine
PKS Cartesian patient coordinate system
$r'_S, \phi'_S, \theta'_S$ updated spherical coordinates of the displaced tip
RR registration routine
$r_S, \phi_S, \theta_S$ spherical coordinates of the tip
S, S' tip
SAR control and analysis routine
sb1-sb6 control commands
ss1-ss6 control signals
T trocar point
T1-T6 first through sixth function keys
TG tangent
TK semi-spherical surface
V axis velocity setpoint values
V0 offset vector
VA vertical axis
w angle of inclination
$w_O$ offset angle
$w_S$ set angle of inclination
X, Y, Z coordinates of the axes in the Cartesian reference coordinate system
x, y, z coordinates of the Cartesian patient coordinate system
X', Y', Z' updated coordinates of the Cartesian reference coordinate system
$x'_S, y'_S, z'_S$ updated Cartesian coordinates of the displaced tip
X0, Y0, Z0 coordinates of the offset vector
$x_S, y_S, z_S$ Cartesian coordinates of the tip
$x_T, y_T, z_T$ Cartesian coordinates of the trocar point

What is claimed is:

1. A surgery assistance system for guiding a surgical instrument, comprising an endoscope, the surgery assistance system comprises an arm system comprising an instrument mount and a control apparatus provided for controlling said arm system, control apparatus is connected to a computer system (CS) connected to a control element (BE), the computer system is for guiding the surgical instrument based on manual actuation of at least one function key (T1-T6), whereby at least the tip (S) of the surgical instrument can be moved in a controlled manner by means of the arm system in a Cartesian patient coordinate system (PKS) and at least one of the three spatial axes (x, y, z) of the Cartesian patient coordinate system (PKS) extends through a surgical opening or a trocar point (T) receiving the surgical instrument, wherein a control and analysis routine (SAR) is provided, which is for determining an angle of inclination (w) of the surgical instrument in relation to the spatial axis (z) of the Cartesian patient coordinate system (PKS) extending through the trocar point (T) and for comparing the angle of inclination (w) so determined with a predetermined set angle of inclination ($w_S$), whereby if the determined angle of inclination (w) exceeds the set angle of inclination ($w_S$) the tip (S) of the surgical instrument is guided on a semi-spherical surface (TK) receiving the tip (S) and when the determined angle of inclination (w) is below the set angle of inclination ($w_S$) the tip (S) of the surgical instrument is guided along a tangent (TG) extending through the tip (S) of the surgical instrument on the semi-spherical surface (TK).

2. The surgery assistance system according to claim 1, wherein when the determined angle of inclination (w) exceeds the set angle of inclination ($w_S$), the tip (S) of the instrument is guided on a circular path (KB) which concentrically surrounds the trocar point (T).

3. The surgery assistance system according to claim 1, wherein the coordinates ($x_T, y_T, z_T$) of the zero point or of the origin of the Cartesian patient coordinate system (PKS) are allocated to the trocar point (T).

4. The surgery assistance system according to claim 1, wherein for registration of the surgery assistance system a registration sensor rigidly affixed to the arm system is guided to the trocar point (T) and the coordinates (X, Y, Z) of the axes of the arm system are defined in a Cartesian reference coordinate system (BKS).

5. The surgery assistance system according to claim 3, wherein for calculation of the starting point of the guiding, the coordinates (X, Y, Z) of the axes of the arm system are determined in the Cartesian reference coordinate systems (BKS) and based thereon the current Cartesian coordinates ($x_S, y_S, z_S$) of the tip (S) of the instrument are determined.

6. The surgery assistance system according to claim 5, wherein based on the Cartesian coordinates ($x_S, y_S, z_S$) of the tip (S) of the instrument in the Cartesian patient coordinates system (PKS) the corresponding spherical coordinates ($r_S, \phi_S, \theta_S$) of the tip (S) of the instrument are determined.

7. The surgery assistance system according to claim 6, wherein the angle of inclination (w) is determined by analysis of at least one of the spherical coordinates ($r_S, \phi_S, \theta_S$) of the tip (S) of the instrument.

8. The surgery assistance system according to claim 6, wherein the set position of the tip (S') of the instrument to be approached by means of the arm system of the surgery assistance system, which lies on the semi-spherical surface (TK) or tangent (TG) based on the determined angle of inclination (w), is determined.

9. The surgery assistance system according to claim 8, wherein the set position of the tip (S') of the instrument (3) is determined in the form of updated spherical coordinates ($r'_S, \phi'_S, \theta'_S$).

10. The surgery assistance system according to claim 9, wherein the updated spherical coordinates ($r'_S, \phi'_S, \theta'_S$) of the tip (S') of the instrument are first converted to updated Cartesian coordinates ($x'_S, y'_S, z'_S$) of the patient coordinate system (PKS), from which the updated Cartesian coordinates ($x'_S, y'_S, z'_S$) of the axes of the arm system in the reference coordinate system (BKS) required for control of the arm system of the surgery assistance system are derived.

11. The surgery assistance system according to claim 1, wherein the surgery assistance system is registered by means of a registration routine (RR) in at least one trocar point (T).

12. The surgery assistance system according to claim 11, wherein corresponding axis velocity set values (V) are determined based on the updated Cartesian coordinates (X', Y', Z') of the axes of the arm system.

13. The surgery assistance system according to claim 1, wherein the instrument is inserted via the surgical opening into a patient's body so that the longitudinal axis (L) of the instrument extends through the zero point of the Cartesian patient coordinate system (PKS) and encloses with the z-axis the angle of inclination (w).

14. The surgery assistance system according to claim 1, further comprising a camera system whereby images (B) are generated and are displayed on a monitor unit (ME).

15. The surgery assistance system according to claim 11, whereby an image horizon of the images (B) displayed on the monitor unit (ME) is calibrated prior to minimally invasive surgery, namely by rotating the camera system on its longitudinal axis (L).

16. The surgery assistance system according to claim 12, whereby the image horizon of the images (B) displayed on the monitor unit (ME) remains essentially constant during the minimally invasive surgery.

17. The surgery assistance system according to claim 2, wherein by actuating a first or a second function key (T1, T2) the tip (S) is guided leftward or rightward on a circular path (KB) extending concentrically around the z-axis (z), causing a leftward or rightward movement of the image (B) displayed on the monitor unit (ME).

18. The surgery assistance system according to claim 1, wherein the set angle of inclination ($w_S$) is between 10° and 25°.

* * * * *